(12) United States Patent
Orphanos et al.

(10) Patent No.: US 12,029,448 B2
(45) Date of Patent: *Jul. 9, 2024

(54) GAS SEAL PAD

(71) Applicant: Saphena Medical, Inc., West Bridgewater, MA (US)

(72) Inventors: Mark J. Orphanos, Foxboro, MA (US); Michael Glennon, Norwell, MA (US); Michael Barenboym, West Bridgewater, MA (US)

(73) Assignee: Saphena Medical, Inc., West Bridgewater, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/485,508

(22) Filed: Oct. 12, 2023

(65) Prior Publication Data

US 2024/0041494 A1    Feb. 8, 2024

Related U.S. Application Data

(60) Continuation of application No. 17/668,454, filed on Feb. 10, 2022, now Pat. No. 11,826,073, which is a division of application No. 16/225,049, filed on Dec. 19, 2018, now Pat. No. 11,278,318.

(60) Provisional application No. 62/610,662, filed on Dec. 27, 2017.

(51) Int. Cl.
*A61B 17/34* (2006.01)

(52) U.S. Cl.
CPC ...... *A61B 17/3462* (2013.01); *A61B 17/3423* (2013.01); *A61B 17/3439* (2013.01); *A61B 17/3474* (2013.01); *A61B 2017/3419* (2013.01); *A61B 2017/3441* (2013.01); *A61B 2017/3492* (2013.01); *A61B 17/3498* (2013.01)

(58) Field of Classification Search
CPC ............ A61B 17/3462; A61B 17/3423; A61B 17/3439; A61B 17/3474; A61B 17/3498; A61B 2017/3419; A61B 2017/3441; A61B 2017/3492; A61F 13/023; A61F 13/0266; A61F 2013/00089
See application file for complete search history.

(56) References Cited

U.S. PATENT DOCUMENTS

| | | | |
|---|---|---|---|
| 5,263,939 | A | 11/1993 | Wortrich |
| 5,667,480 | A | 9/1997 | Knight et al. |
| 5,984,247 | A | 11/1999 | Luhmann et al. |
| 6,811,546 | B1 | 11/2004 | Callas et al. |
| 9,421,034 | B2 | 8/2016 | Hart et al. |
| 11,278,318 | B2 | 3/2022 | Orphanos et al. |

(Continued)

OTHER PUBLICATIONS

PCT International Search Report received in International Application No. PCT/US18/66502 mailed Apr. 1, 2019.

*Primary Examiner* — Michael J Tsai
*Assistant Examiner* — Rachel T. Smith
(74) *Attorney, Agent, or Firm* — Greenberg Traurig, LLP; Chinh H. Pham; Andrew Cull

(57) ABSTRACT

A pad is provided having a body for providing a gas seal over a surgical site, a port extending between a first surface of the body and a second surface of the body and sized accept a surgical instrument, and a lumen situated along the body and having a first opening and a second opening, the second opening aligned with the surgical site for communicating a fluid flow to the surgical site.

20 Claims, 18 Drawing Sheets

(56) References Cited

U.S. PATENT DOCUMENTS

| | | |
|---|---|---|
| 2009/0036918 A1* | 2/2009 | Burgess ................ A61B 90/40 606/201 |
| 2010/0228094 A1 | 9/2010 | Ortiz et al. |
| 2011/0071473 A1 | 3/2011 | Rogers et al. |
| 2011/0301419 A1 | 12/2011 | Craft et al. |
| 2012/0245423 A1 | 9/2012 | Rodrigues |
| 2015/0148613 A1 | 5/2015 | Piskun et al. |
| 2015/0230868 A1 | 8/2015 | Miller |
| 2017/0215917 A1 | 8/2017 | Harrah et al. |
| 2019/0192188 A1 | 6/2019 | Orphanos et al. |
| 2022/0265315 A1 | 8/2022 | Orphanos et al. |

\* cited by examiner

404

404b

404a

GAS SEAL PAD

CROSS-REFERENCE TO RELATED APPLICATION(S)

This application is a continuation patent application of U.S. application Ser. No. 17/668,454, filed Feb. 10, 2022, which is a divisional patent application of U.S. application Ser. No. 16/225,049, filed Dec. 19, 2018, now U.S. Pat. No. 11,278,318, which claims priority to and the benefit of U.S. Provisional Application No. 62/610,662, filed Dec. 27, 2017, the disclosures of each of which are hereby incorporated by reference in their entireties.

TECHNICAL FIELD

Example embodiments relate generally to surgical devices and more particularly to apparatuses for providing a substantially gas tight seal at a site of incision.

BACKGROUND

Conventionally, trocars are inserted into a surgical site of a patient to serve as a portal for subsequent introduction of insufflation gas and/or placement of other instruments into the surgical site. However, conventional trocars are large, awkward, and difficult to accurately insert and place within the patient.

SUMMARY

In some embodiments, an apparatus is provided. The apparatus can include a body for providing a gas seal over a surgical site, a port extending between a first surface of the body and a second surface of the body and sized to accept a surgical instrument, and a lumen situated along the body and having a first opening and a second opening, the second opening aligned with the surgical site for communicating a fluid flow to the surgical site. The apparatus can further include one of a flap, septum, a one-way valve, or combinations thereof for sealing the port. The port can be sized to form a gas seal with the surgical instrument. The apparatus can further include a tube extending from the second opening of the lumen toward the surgical site to enhance delivery of the fluid flow to the surgical site. The tube can extend through the lumen. The apparatus can further include a tab extending from the body to provide a finger grip to facilitate removal of the pad. The apparatus can further include an adhesive disposed over the at least a portion of the second surface of the body to aid in forming the gas seal over the surgical site.

In some embodiments, a method is provided. The method includes placing pad over a surgical site to form a gas seal between the pad and the surgical site, the pad having a port in alignment with the surgical site, inserting a surgical instrument through the port into the surgical site while maintaining a gas-sealed engagement with the surgical instrument, and communicating a fluid flow through the pad into the surgical site. The step of communicating can include introducing the fluid flow from a fluid source to a first opening of a lumen and exiting the fluid flow from a second opening of the lumen. The fluid flow can include an insufflation gas. The step of communicating can include insufflating the surgical site with the insufflation gas. The step of placing can include adhering, by an adhesive disposed over at least a portion of a surface of the pad over the surgical site. The method can further include grasping and pulling a tab extending from the pad to remove the pad from the surgical site. The method can further include advancing a tip of the surgical instrument to a target anatomical structure.

In some embodiments, a method of endoscopic vessel harvesting is provided. The method includes placing a pad over an incision at a surgical site to form a gas seal between the pad and the surgical site, the pad having a port in alignment with the incision, inserting an endoscopic vessel harvester through the port into the incision while maintaining a gas-sealed engagement with the endoscopic vessel harvester, insufflating the surgical site by introducing gas flow into the incision, and harvesting a target vessel using the endoscopic vessel harvester.

The step of placing can include adhering, by an adhesive disposed over at least a portion of a surface of the body, the pad over the surgical site. The method can further include grasping and pulling a portion of the body to remove the pad from the surgical site. The method can further include advancing a tip of the surgical instrument to a target anatomical structure. The method can further include cutting the incision at the surgical site. The method can further include dissecting to a depth of a target vessel. The introducing the insufflation gas flow from the fluid source can be through the port in the body into the incision.

In some embodiments an apparatus is provided. The Apparatus can include a body for providing a gas seal over a surgical site, a sealing member extending through the body, the sealing member having a first opening and a second opening through which a surgical device can be directed into the surgical site, and a channel along the body having a first opening at one end of the channel and a second opening at an opposing end of the channel in fluid communication with the sealing member. The apparatus can further include a stiffener situated within the sealing member to provide reinforcement to the sealing member. The stiffener can include one or more geometric protrusions extending therefrom to provide a bonding surface for the body and the stiffener. The first opening and the second opening can be sized to form a gas seal with the surgical instrument inserted therethrough. The apparatus can further include an adhesive disposed over the at least a portion of the second surface of the body to aid in forming the gas seal over the surgical site.

BRIEF DESCRIPTION OF THE DRAWINGS

Illustrative, non-limiting example embodiments will be more clearly understood from the following detailed description taken in conjunction with the accompanying drawings.

DETAILED DESCRIPTION OF THE EMBODIMENTS

Figure 1A:
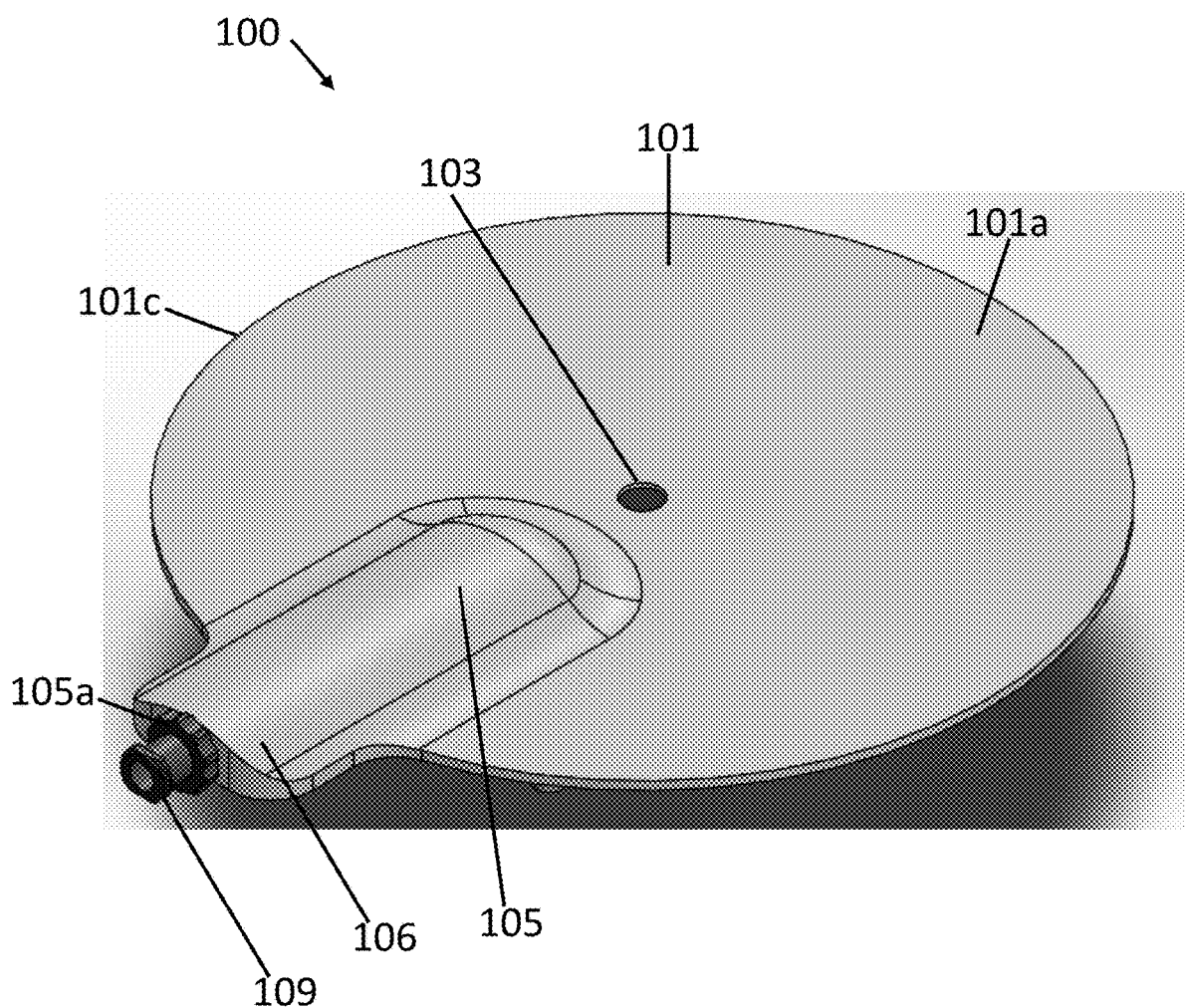
FIGS. 1A, 1B, AND 1C are perspective, side, and bottom views of a sealing device in accordance with various embodiments.

Various exemplary embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. Like numerals refer to like elements throughout.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Embodiments of the present disclosure generally apply to surgical instruments. The various embodiments of the present disclosure can be used, for example, to provide a flexible, gas-sealed sealing device for obviating the need for a trocar during an endoscopic procedure.

Figure 1B:
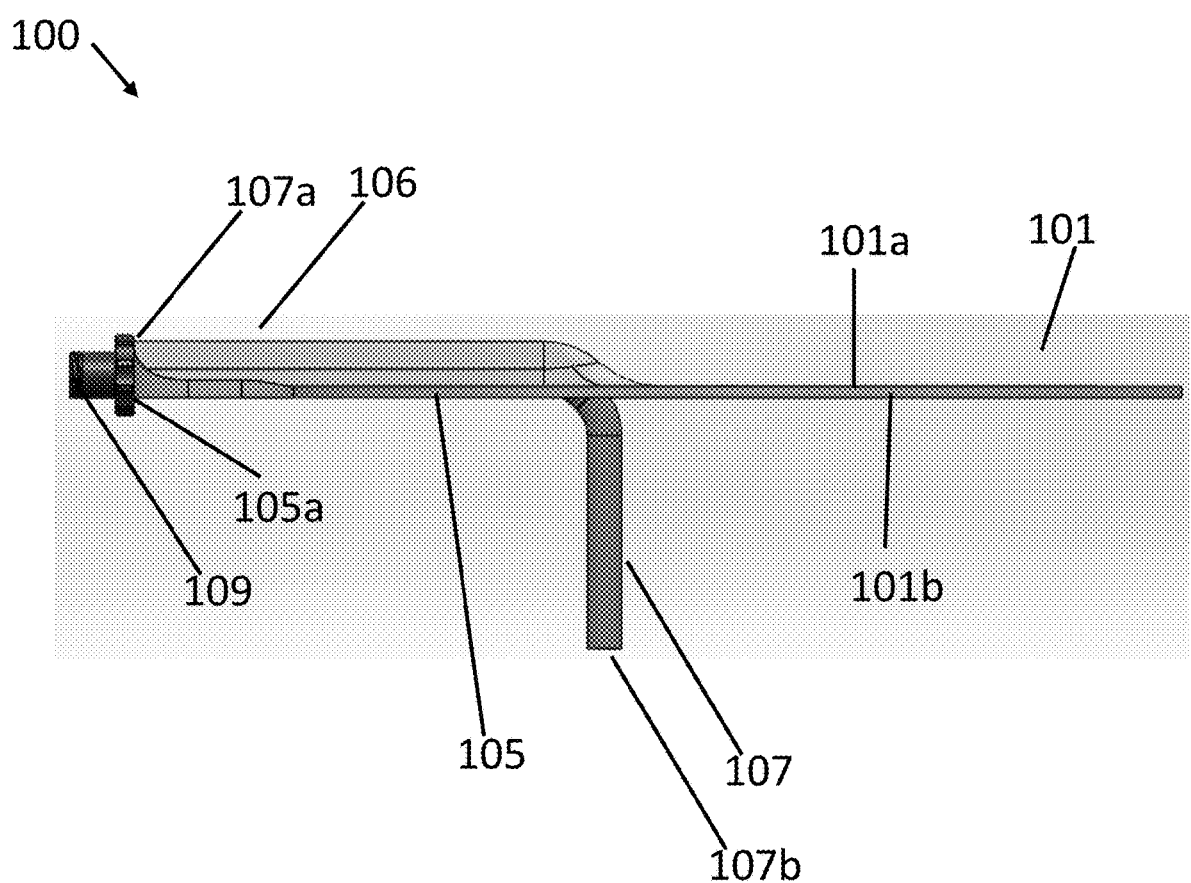
Figure 1C:
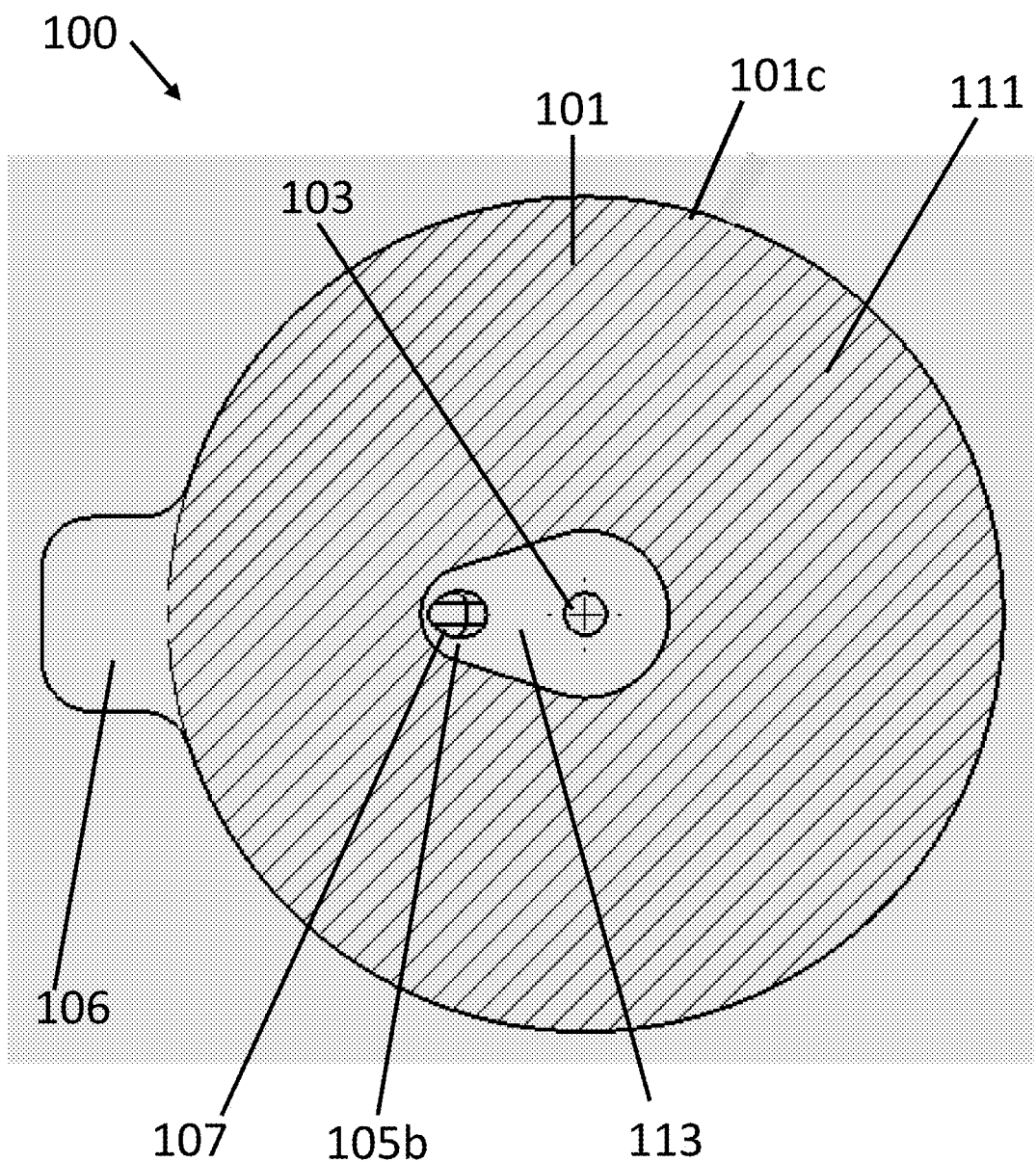

FIGS. 1A-1C illustrate a sealing device or apparatus 100, such as a pad for placement at a surgical site to create a substantially tight gas seal. For example, the gas seal can be a substantially gas-tight seal. Referring first to FIG. 1A, pad 100, in accordance with various embodiments of the present disclosure, can include a body 101 having a first surface 101a and a second surface 101b for placement at a surgical site over, for instance, an incision. To facilitate formation of the substantially gas-tight seal, the body 101 can be sufficiently bigger than the surgical site so as to completely cover the incision. In one embodiment, the body 101 can be circular in shape with a diameter sufficiently larger than the incision and large enough to provide sufficient surface area to adhere to the target site, while not being overly cumbersome for a particular application site. For example, the diameter of the body 101 can be 3-5 inches. The body 101 can also be sized and shaped to allow for mobility while maintaining adhesion to a target site, for example, at a knee or elbow. Although shown in FIG. 1A as having a substantially circular shape, it will be apparent in view of this disclosure that the body 101 can be any shape including, for example, square, rectangular, hexagonal, triangular, octagonal, oval, a cross, any geometric design, any other suitable shape, or combinations thereof, so long as the body is capable of covering the incision to form a gas-tight seal. In some embodiments, the body 101 can have a diameter between about 1" to about 10" to facilitate covering the incision to form a gas-tight seal. However, it will be apparent in view of this disclosure that any size body 101 or device 100 capable of covering the incision to form a gas-tight seal can be used in accordance with various embodiments.

To the extent it is desirable for the device 100 to conform to the patient's body topography to aid in forming the gas seal, in some embodiments, the body 101 can be sufficiently flexible for conforming to surface of the patient at the surgical site. In this regard, as shown in FIGS. 1A-1B, the body 101 can be substantially thin to promote flexibility of the device 100. In one embodiment, the body can be provided with a thickness ranging from about 0.01" to about 1.0" thick. Of course, the thickness of the body can be provided with a range outside the noted range depending on the application. In addition, the body 101 can be from a substantially fluid impermeable material to provide a gas barrier over the surgical site. Examples of such a material can include, for example, polyurethane, an elastomer such as silicone, EPDM, Flourocarbon, Neoprene, Nitrile, a polymer such as Polyurethane, Polyethelyne, Polyproplyne, Polystyrene, PET, PTFE, PFA, FEP, EVA, bioresorables (PLA, PGA, PCL), any other suitable material, or combinations thereof. In one embodiment, wherein the device is to be placed against the skin or other tissue, the material from which the device can be made may be biocompatible. In some embodiments, the material of the body 101 can also advantageously be tear resistant to prevent inadvertent destruction or leakage. For example, in some embodiments, the body 101 can have a durometer hardness of about Shore 10A to about Shore 90A.

Referring again to FIG. 1A, the body 101 can also include a port 103 extending from one of the first surface 101a to the second surface 101b to function as a portal for introducing one or more surgical instruments into the patient at the surgical site on incision location. In some embodiments, the port 103 can be sized to be slightly smaller than a diameter of the surgical instrument being inserted. To that end, the port 103 can provide a substantially tight, elastically gas-sealed fit with the surgical instrument. In some embodiments, the port 103 can be substantially centrally located within the body 101. However, it will be apparent in view of this disclosure that the port 103, in accordance with various embodiments, can be located anywhere within the body 101. In some embodiments the port 103 can be provided with a resealable element (not shown) such as, for example, a resealable flap, a resealable septum, a one-way valve, or combinations thereof to provide gas-sealing of the port 103 when no surgical instrument is present therein while permitting insertion of one or more surgical instruments. In some embodiments, the resealable element can prohibit ambient airflow into the patient via the port 103 and prevent escape of insufflation gas through the port 103. Thus, the gas seal created by the body 101 is maintained regardless of the presence of a surgical instrument in the port 103.

Still referring to FIG. 1A, the body 101 can also include, in one embodiment, a tunnel or lumen 105 for delivering a fluid flow through the device 100 and into the surgical site. The lumen 105, as illustrated, includes a first opening 105a at one end for receiving a fluid flow from a fluid source. The lumen 105, as illustrated, also includes a second opening 105b at an opposite end aligned with the surgical site for delivering the fluid flow thereto. For example, the lumen 105 can extend radially inward from an edge 101c of the body 101 toward the port 103. In some embodiments, the lumen 105 can extend from the first opening 105a positioned anywhere on the first surface 101a or the edge 101c of the body 101 to the second opening 105b positioned anywhere on the second surface 101b of the body 101 suitable for delivering the fluid flow to the surgical site. In accordance with various embodiments, the first opening 105a can be connected to a coupling fitting 109 for permitting the fluid source (e.g., a gas insufflation supply, a saline supply, a water supply, a syringe, or any other such device or equipment) to be connected to the lumen 105 for communicating a gas or other fluid into or out of the patient via the lumen 105. In some embodiments, the fluid source can be provided through the port 103 and/or the lumen 105. The coupling fitting 109 can include any combination of coupling mechanisms for attaching another device to the device 100, for example, the coupling fitting 109 can be a Luer fitting. The coupling fitting 109 can be made from any combination of materials, for example, metal, plastic, etc. and can be fixedly or removably attached to the body 101.

In some embodiments, the body 101 can be configured for distal insufflation such that the fluid source can be provided through a lumen in a medical instrument separate from the device 100. For example, the medical instrument can provide the fluid source through the port 103 or through a separate point of entry.

To facilitate removal of the device 100, in one embodiment, the body can be provided with a tab 106 extending radially outward from the edge 101c of the body 101. In some embodiments, the tab 106 can form a finger grip for aiding a user in removing the device 100 from the patient. As shown in FIG. 1A, in one embodiment, tab 106 can be provided as an extension of lumen 105. However, it will be apparent in view of this disclosure that, in accordance with various embodiments, the device 100 may be designed without a tab 106 or with a tab 106 that is separate from the lumen 105.

To the extent desired, a fluid conduit such as tube 107 can be provided extending through the lumen 105. In an embodiment, as illustrated in FIG. 1B, the tube 107, can extend through the lumen 105 between a first end 107a and a second end 107b. To maintain the gas seal between the device 100 and the surgical site, in some embodiments, the tube 107 can form a gas seal (e.g., by welding, adhesive, or elastomeric interference fit) with the lumen 105. As shown in FIG. 1B, in some embodiments, the second end 107b of the tube 107 can extend beyond the second opening 105b of the lumen 105. However, in some embodiments, the second end 107b can, for example, be flush with the second opening 105b or terminated within the lumen 105 so as to position the second end 107b over or above the surgical site. In an alternative embodiment, the first end 107a of the tube 107 can be coupled to the second opening 105b of the lumen 105 and extend therefrom. In such an embodiment, the first end 107a of the tube 107 can form a gas seal (e.g., by welding, adhesive, or elastomeric interference fit) with the second opening 105b of the lumen 105. More generally, any relative configuration of the tube 107 and the lumen 105 capable of delivering a fluid to the surgical site can be used in accordance with various embodiments. The tube 107 can be sized and shaped to all passage through intermediary layers (e.g., skin, fat, etc.) to a target location (e.g., vessel). For example, the tube 107 can be ½ inches long to 2 inches long, however, these dimensions can vary based on the particular application and the target location.

As shown in FIG. 1B, to provide enhanced delivery of the fluid into the surgical site, the second end 107b can extend out of the second opening 105b of the lumen 105 for a predetermined distance into the patient. Because different surgical procedures, different patients, and different anatomical structures can require incisions of varying depth, n some embodiments, the tube 107 can be trimmable so as to permit customization of the predetermined distance the tube 107 extends into the patient.

For maintaining the gas seal provided by the body 101 over the surgical incision, the tube 107, in one embodiment, can be sufficiently flexible to permit bending of the tube 107 with the body 101. In one embodiment, the tube 107 can further be sufficiently rigid to permit advancement of the tube 107 into the patient and to prevent crushing and/or occlusion of the tube 107. To that end, in some embodiments, the tube 107 can be constructed of, for example, PVC, Tygon, Silicone, PET, Polyurethane, any other suitable material, or combinations thereof.

In accordance with various embodiments, the first end 107a of the tube can be coupled to the coupling fitting 109 for permitting the fluid source (e.g., a gas insufflation supply, a saline supply, a water supply, a syringe, or any other such device or equipment) to be connected to the tube 107 for communicating a gas or other fluid into or out of the patient via the tube 107.

However, it will be apparent in view of this disclosure that, in some embodiments, the device 100 may not include a tube 107. In such embodiments the lumen 105 itself can provide passage for the gas or other fluid into or out of the patient. Additionally, in such embodiments, the coupling fitting 109 can be directly attached to the device 100 at the first opening 105a. In some embodiments, the second end 107b and the port 103 can be the same opening.

Referring now to FIG. 1C, to form a gas seal and to maintain a position of the device 100 following placement on the patient, an adhesive 111 can be disposed on at least a portion of the second surface 101b of the body 101 and protected by a removable liner. In some embodiments, the adhesive 111 can be selected to permit multiple adhere-remove cycles for repositioning of the body 101 on the patient. For example, the adhesive 111, in some embodiments, can include any suitable medical adhesive such as, for example, a silicone gel adhesive, Acrylic adhesive, or polyurethane adhesive. Although described herein as having an adhesive 111, it will be apparent in view of this disclosure that any material or surface treatment suitable for promoting gas-sealed engagement between the patient and the device 100 can be used in accordance with various embodiments. As would be appreciated by one skilled in the art, an adhesive can be applied separately from the body 101 and adhere the body 101 to the patient without departing from the scope of the present invention.

In some embodiments, the adhesive 111 can be selectively omitted from portions of the second surface 101b. Still referring to FIG. 1C, in some embodiments, an adhesive-free zone 113 is provided surrounding the port 103 and the second opening 105b. By omitting the adhesive 111 in the adhesive-free zone 113, the body 101 is permitted to be locally laterally displaced. Thus, any surgical instrument inserted through the port 103 can be laterally displaced as needed to position and manipulate the instrument during a procedure. Furthermore, because the adhesive-free zone 113 permits the pad material surrounding the port 103 to stretch relative to the patient's skin, the gas-sealed fit between the body 101 and the surgical instrument can be maintained. By contrast, absent the adhesive-free zone 113, the adhesive 111 would be locally retained on the skin and thus movement of the surgical instrument would create separation between the instrument and the body 101, thereby causing a gas leak. The adhesive 111 can also omitted from the tab 106 for aiding a user in removing the device 100 after use. By omitting the adhesive 111 on the tab 106, the finger grip formed by the tab 106 does not adhere to the patient during use or the user during removal and can thus be readily grasped by the user for removing the device 100.

Figure 2A:
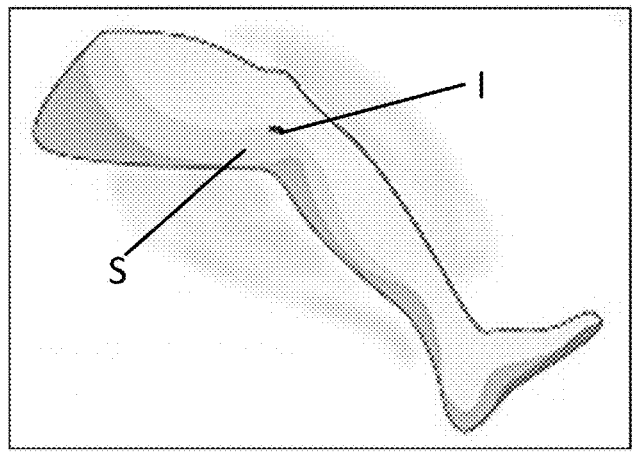
FIGS. 2A, 2B, 2C, 2D, 2E, AND 2F are diagrams illustrating steps for a method of using the sealing device of FIGS. 1A-1C in accordance with various embodiments.
Figure 2B:
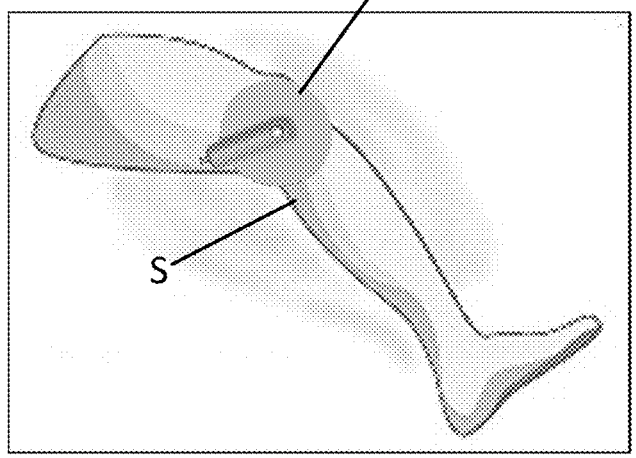

Referring now to FIGS. 2A-2F, a method for using the device 100 is provided. As shown in FIG. 2A, the user can place an incision I in the skin S. In some embodiments, such as, for example, a cut-down procedure, the user can continue to dissect to a targeted surgical site. For example, in connection with an endoscopic vessel harvesting procedure, the user can dissect until a targeted vessel is found. Referring now to FIG. 2B, the adhesive 111 of the body 101 can be placed onto the skin S such that the port 103 of the device 100 is positioned over the incision site, thereby forming a gas seal between the device 100 and the patient. The second end 107b of the tube can also be fed into the incision site to a desired depth. Although FIGS. 2A and 2B show formation of the incision I prior to placement of the device 100 on the skin S, it will be apparent in view of this disclosure that, in some embodiments, the device 100 can be placed prior to forming the incision I. For example, where the device 100 includes the lumen without the tube 107, the device 100 can be placed and the incision I can be formed through the port 103.

Figure 2C:
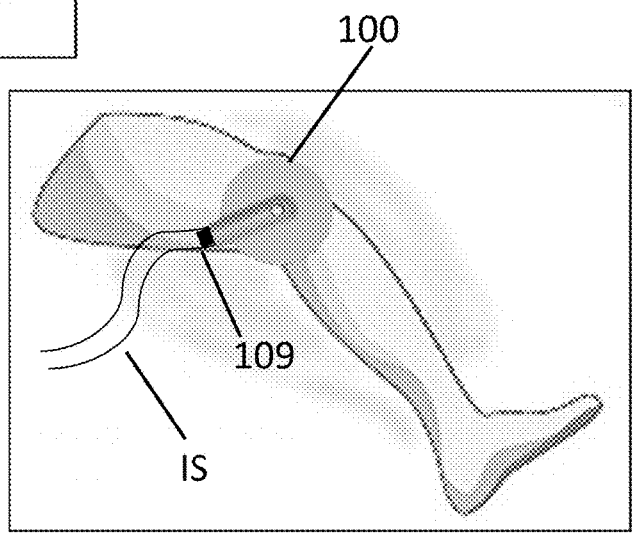
Figure 2D:
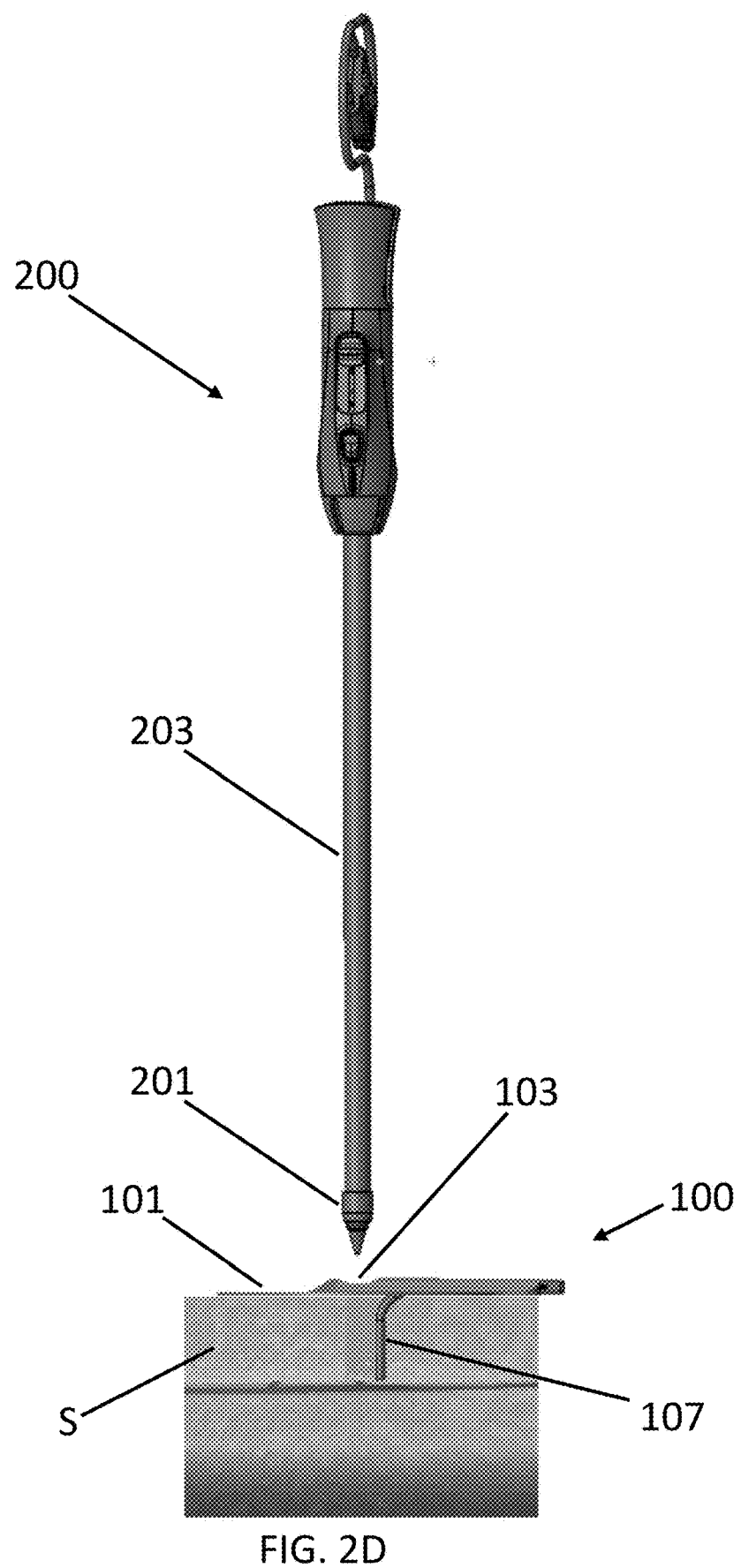
Figure 2E:
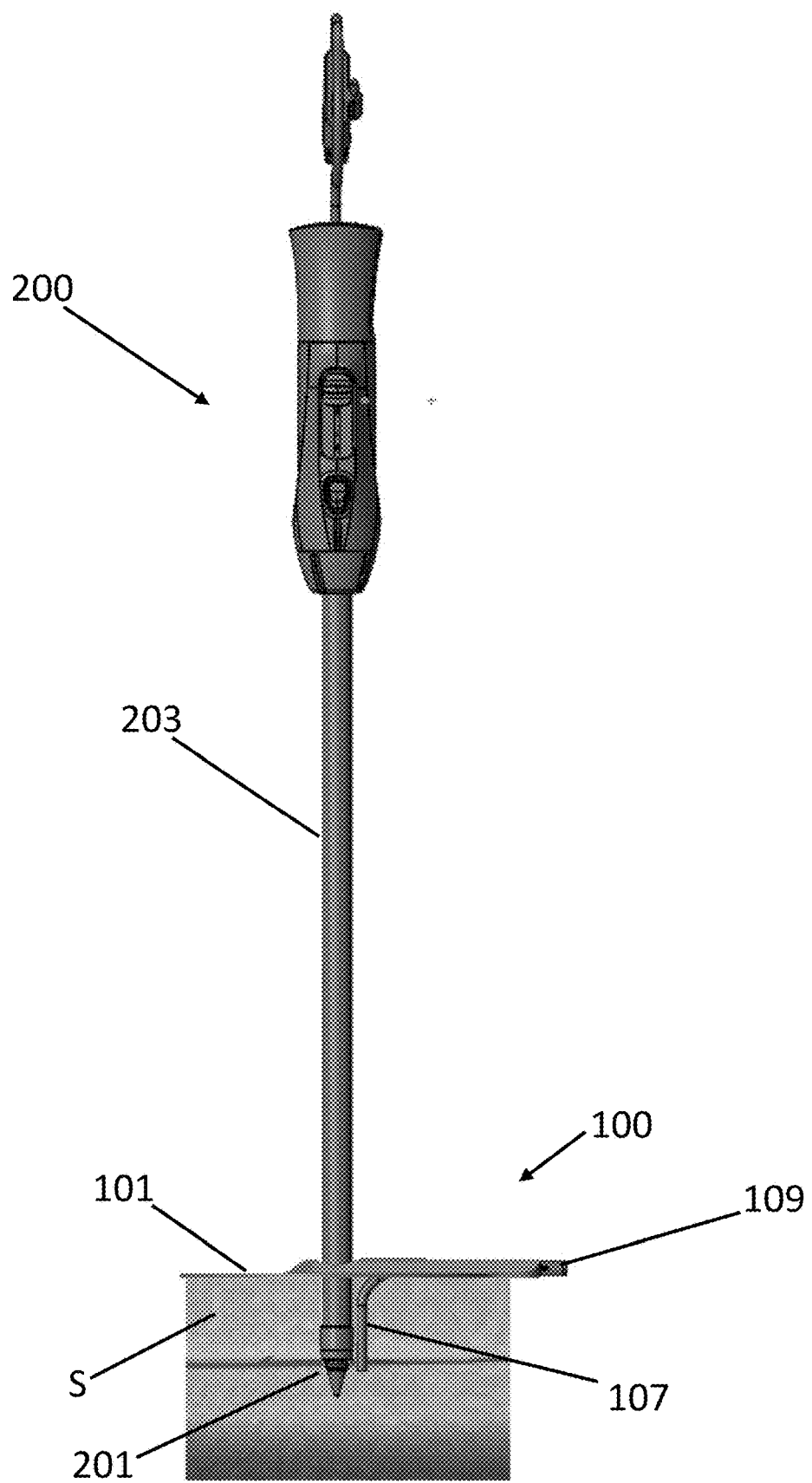
Figure 2F:
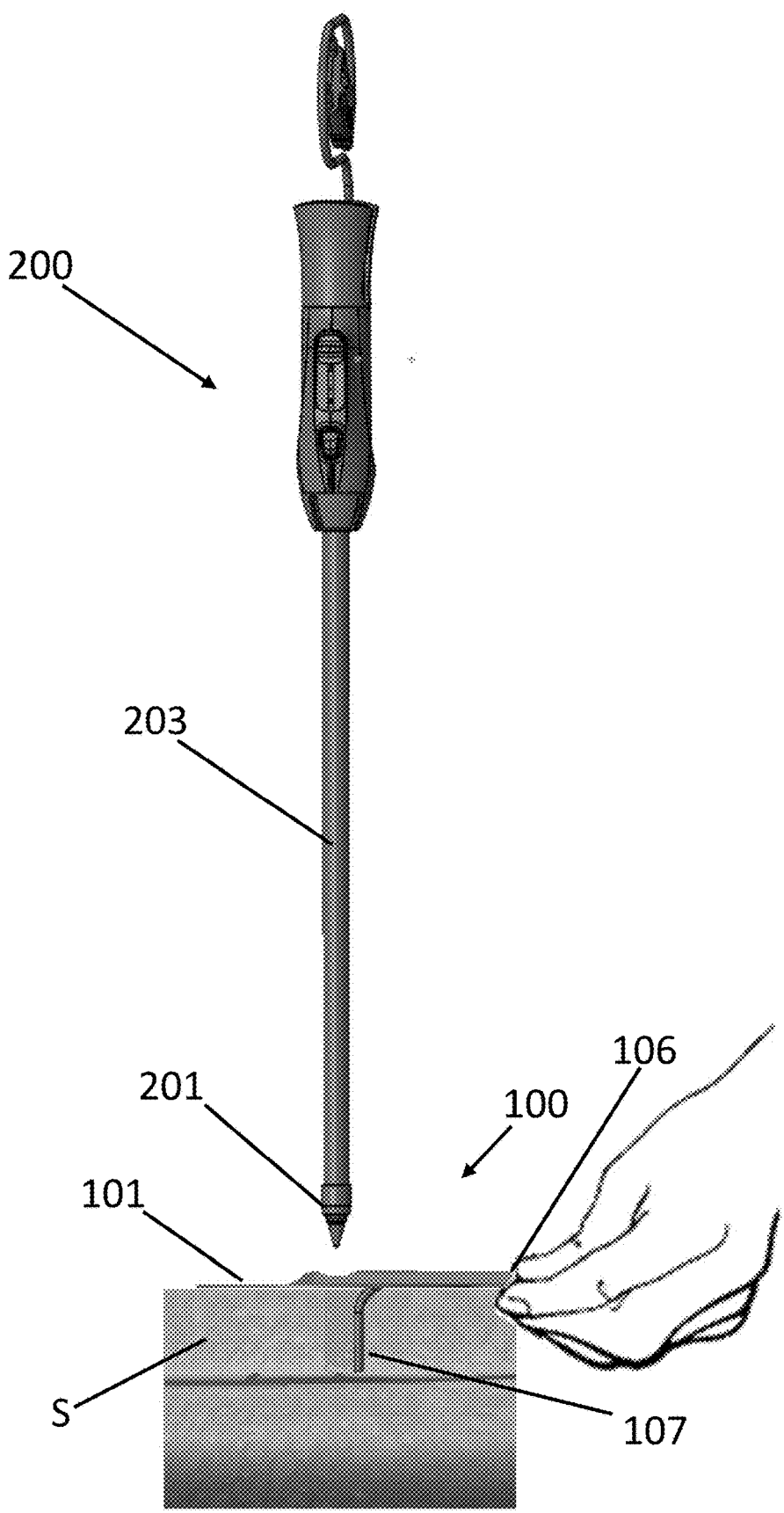

Once the gas seal is formed between the device 100 and the incision site, as shown in FIG. 2C, the insufflation supply IS can be connected to the lumen 105 or the tube 107 (e.g., via coupling fitting 109 as shown) to communicate insufflation gas into the surgical site. As shown in FIG. 2D, a tip 201 and shaft 203 of a surgical instrument 200 (e.g., an EVH as shown) can be inserted through the port 103 to form a gas-sealed fit with the body 101. The surgical instrument 200, as shown in FIG. 2E, can then be advanced to the surgical site and used to perform a surgical procedure such as harvesting a vessel in connection with an EVH procedure. As shown in FIG. 2F, the surgical instrument 200 can be withdrawn from the port 103 and the device 100 can be removed from the patient's skin S (e.g., by grasping and pulling on tab 106). Although described in a particular order herein, it will be apparent in view of this disclosure that the steps of placing an incision I, cutting down, placing the device 100, insufflating the surgical site, inserting the surgical instrument 200, and withdrawing the surgical instrument 200 can be performed in any order as appropriate for a particular medical procedure.

Figure 3A:
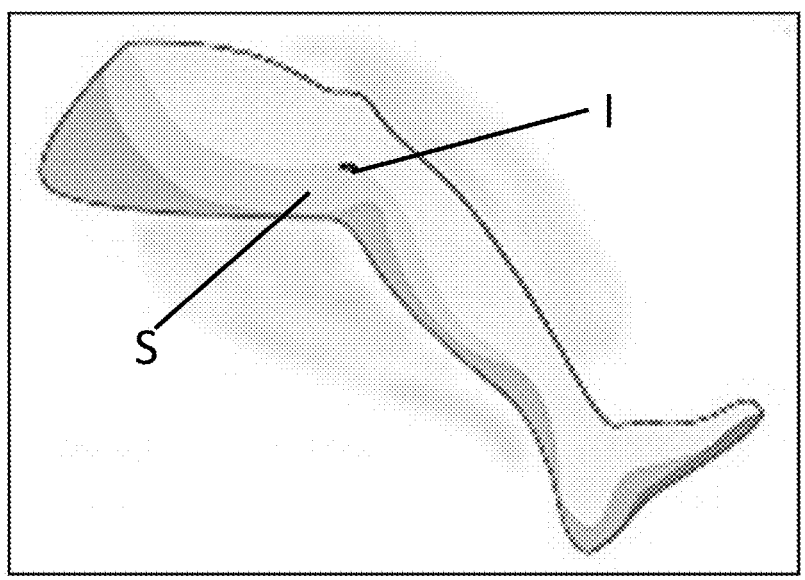
FIGS. 3A, 3B, 3C, 3D, 3E, 3F, AND 3G are diagrams illustrating steps for another method of using the sealing device of FIGS. 1A-1C in accordance with various embodiments.
Figure 3B:
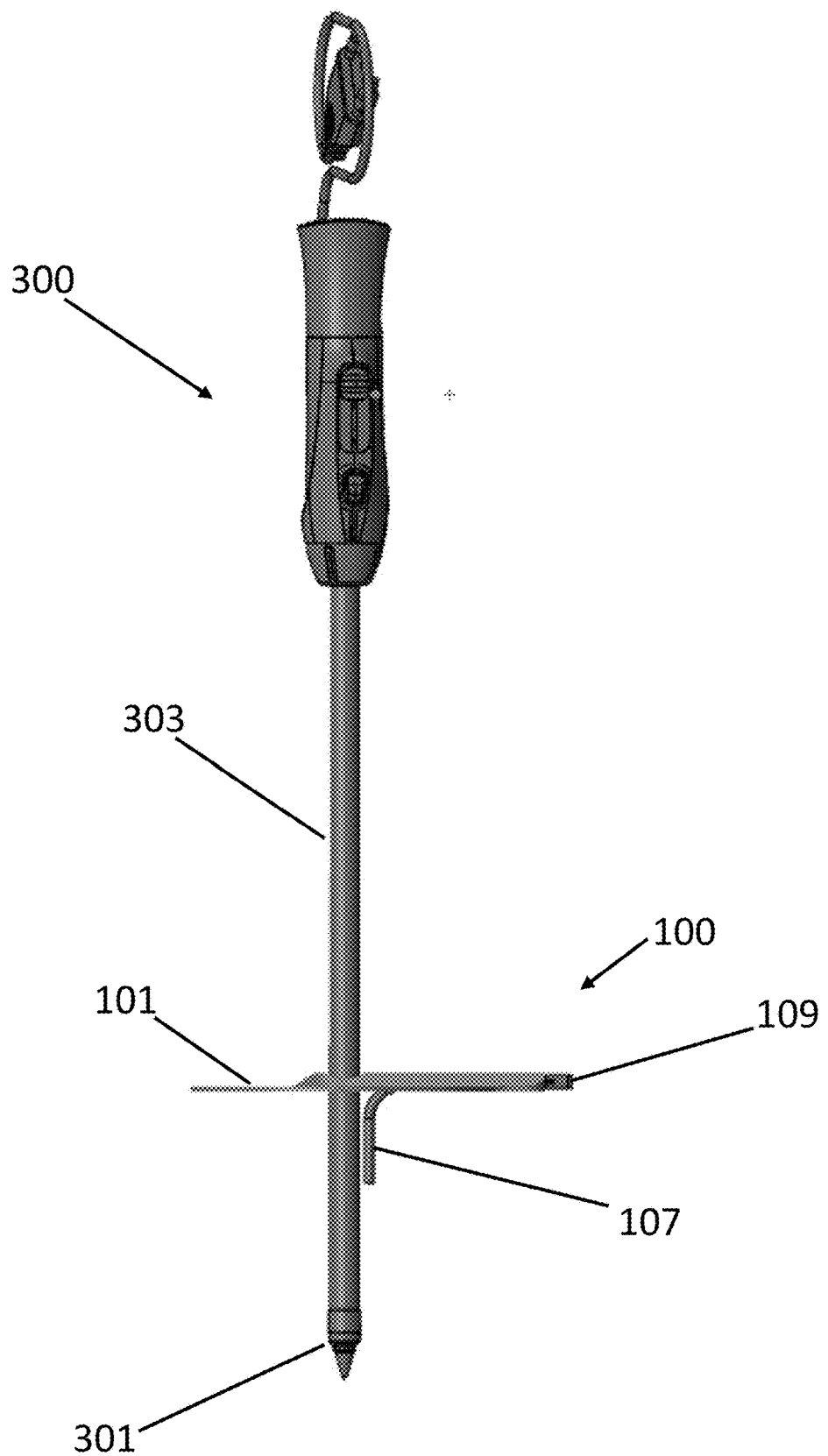
Figure 3C:
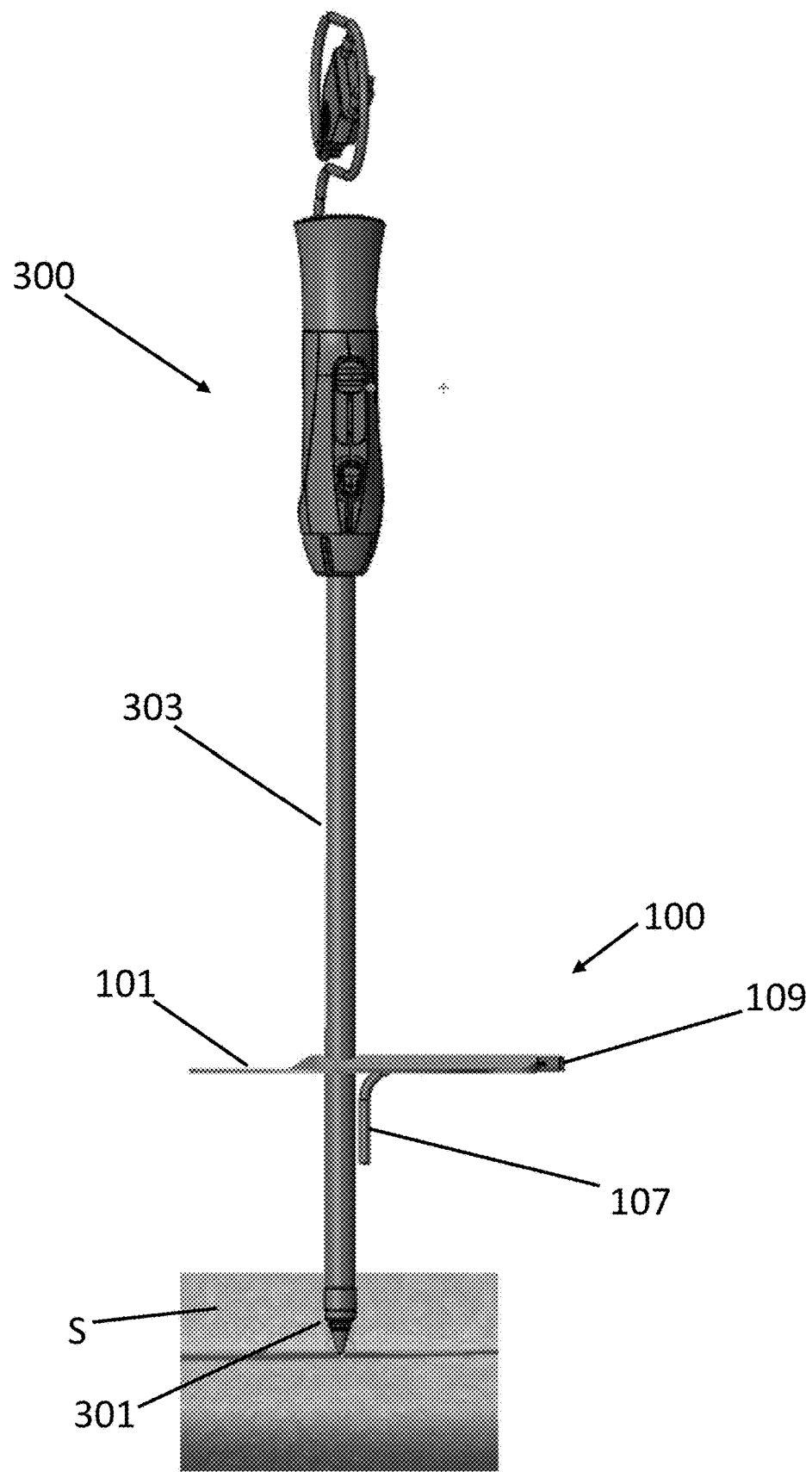
Figure 3D:
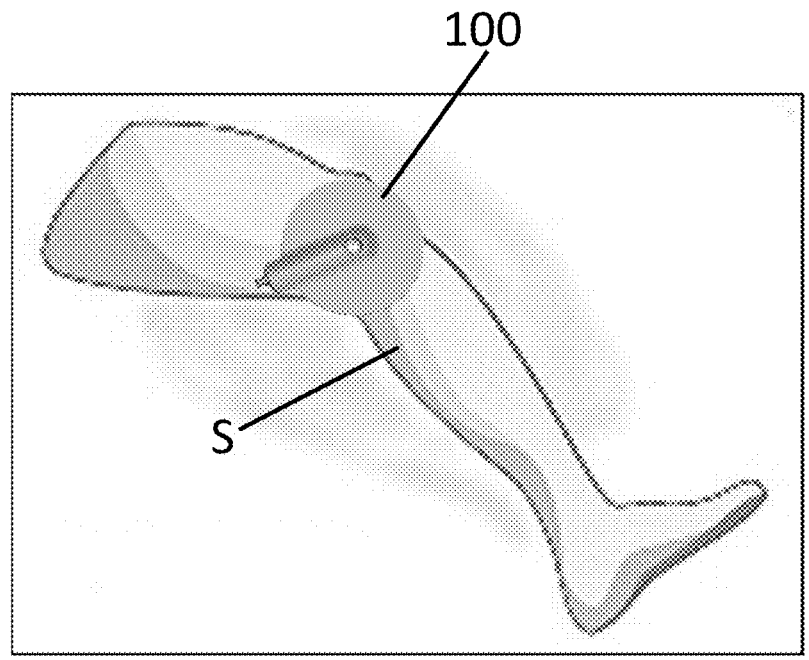

Referring now to FIGS. 3A-3F, an alternative method for using the device 100 is provided. As shown in FIG. 3A, the user can place an initial incision I in the skin S. Referring now to FIG. 3B, in some embodiments, such as, for example, a tip-search technique procedure, the user can insert a tip 301 of a surgical instrument 300 (e.g., an EVH as shown) through the port 103 of the device 100 to form a gas seal between the device 100 and the surgical instrument 300. As shown in FIG. 3C, the user can advance the tip 301 and at least a portion of a shaft 303 of the surgical instrument 300 into the patient via the incision until the desired surgical site is reached (e.g., a targeted vessel for harvesting). As shown in FIG. 3D, the adhesive 111 of the body 101 can then be placed onto the skin S to form a gas seal between the patient and the device 100, wherein the port 103 is positioned over the incision I. The second end 107b of the tube can also be fed into the incision site to a desired depth.

Figure 3E:
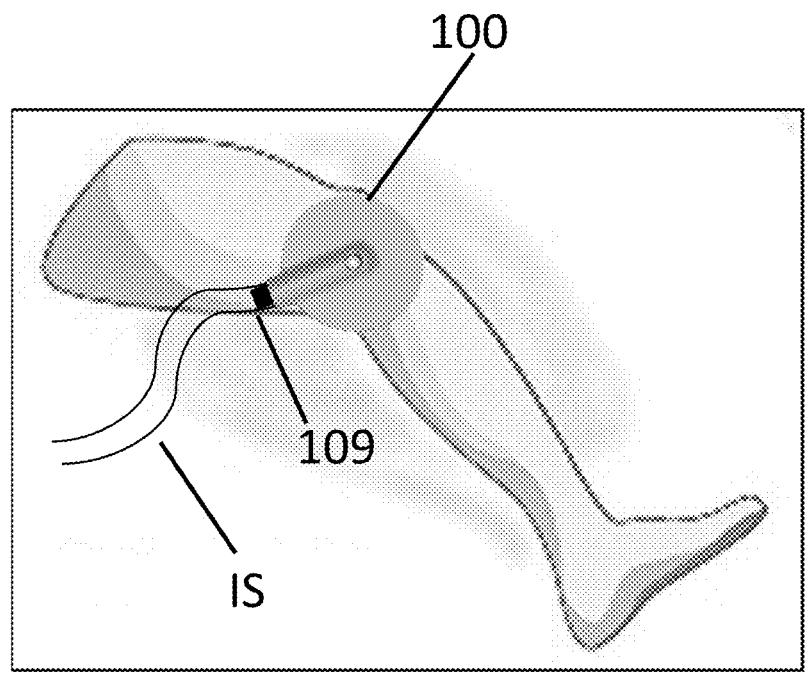
Figure 3F:
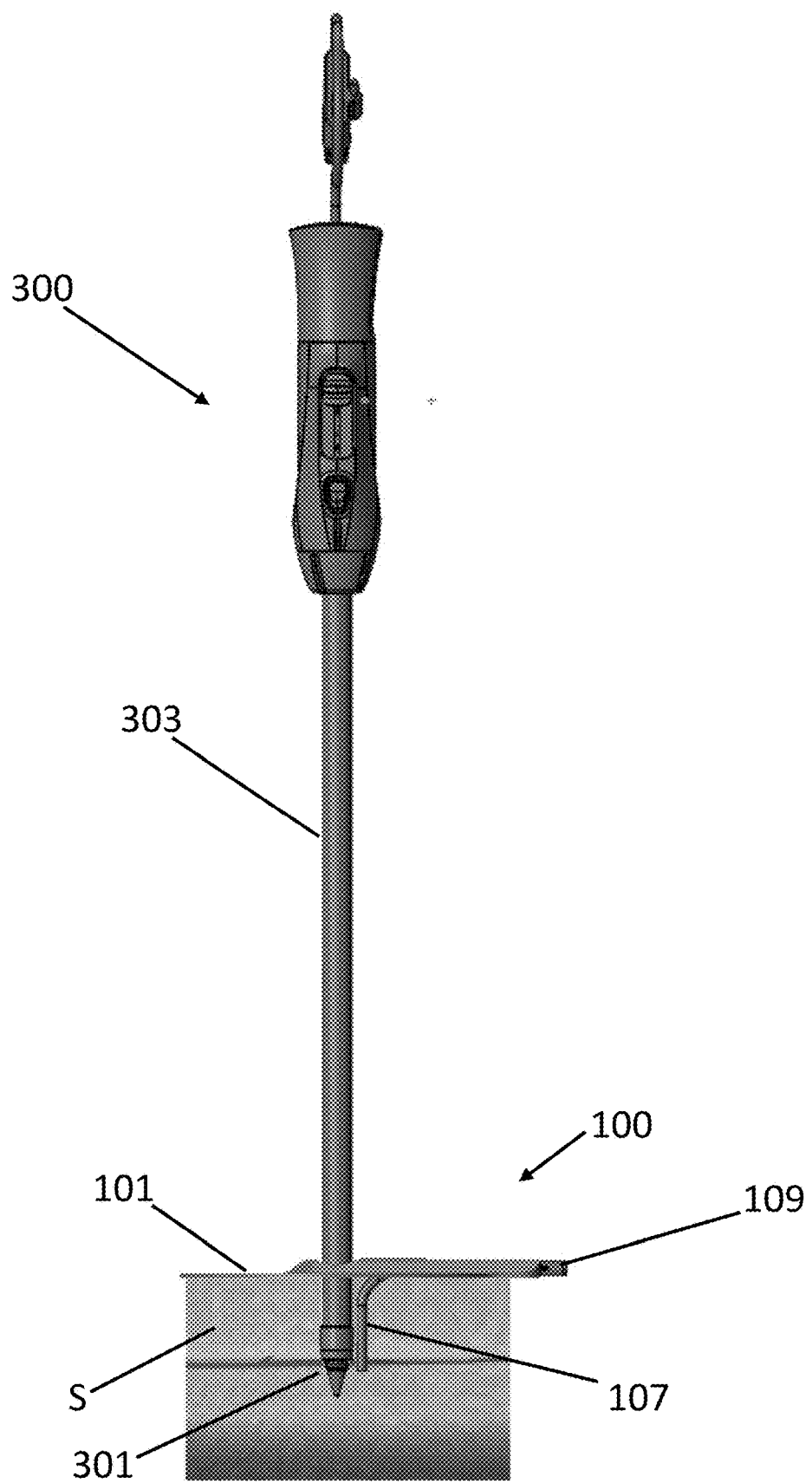
Figure 3G:
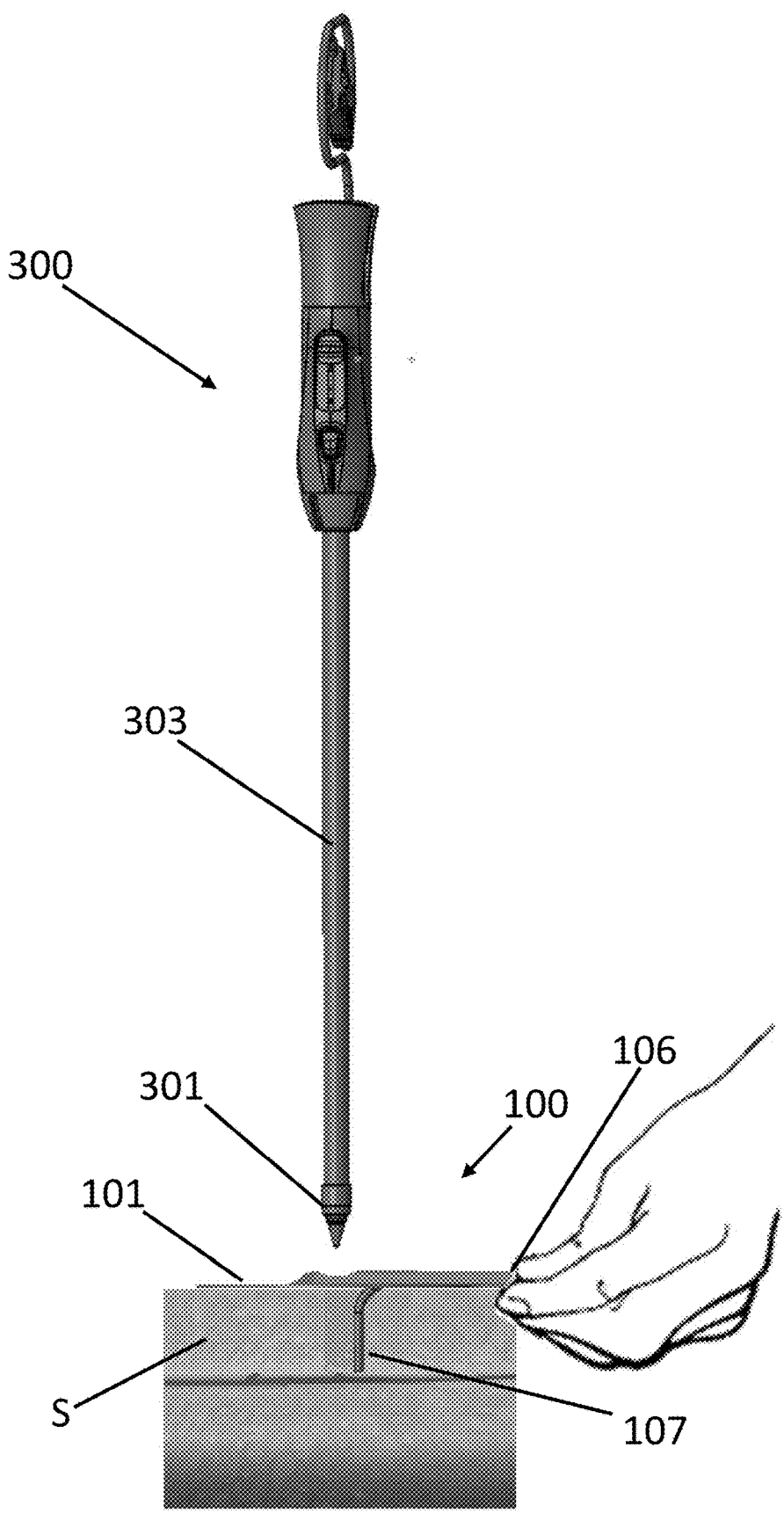

At FIG. 3E, once the gas seal is formed between the device 100 and the incision site, the insufflation supply can be connected to the lumen 105 or the tube 107 (e.g., via coupling fitting 109 as shown) to communicate insufflation gas into the surgical site. As shown in FIG. 3F, the surgical instrument 300 can be used to perform a surgical procedure such as harvesting a vessel in an EVH procedure. As shown in FIG. 3G, after completion of the procedure, the surgical instrument 300 can be withdrawn from the port 103 and the device 100 can be removed from the patient's skin S (e.g., by grasping and pulling on tab 106). Although described in a particular order herein, it will be apparent in view of this disclosure that the steps of placing an incision I, inserting the tip 301 through the port 103, advancing the tip 301 into the patient until reaching the surgical site, placing the device 100, insufflating the surgical site, and withdrawing the surgical instrument 300 can be performed in any order as appropriate for a particular medical procedure.

Figure 4A:
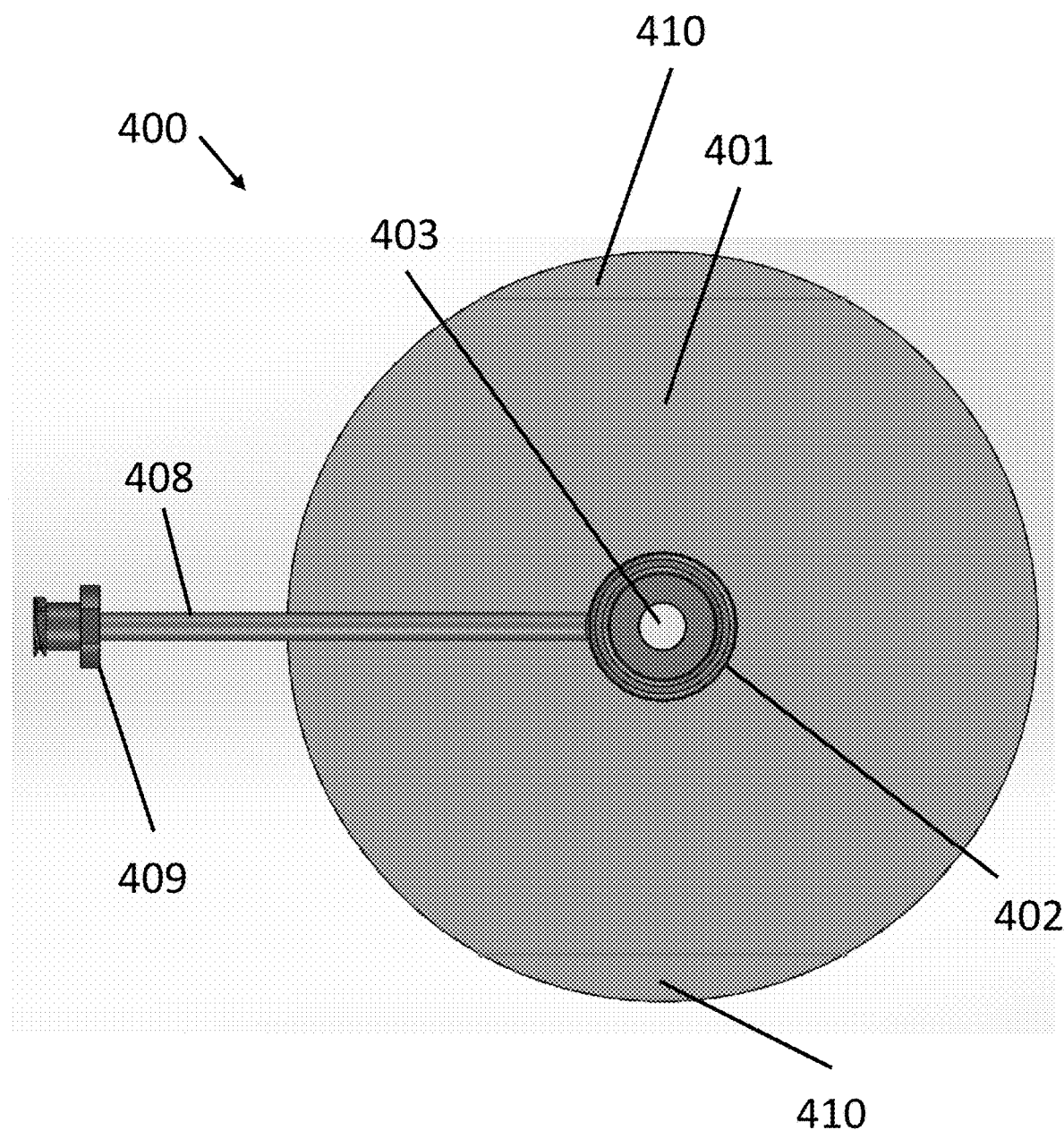
FIGS. 4A, 4B, 4C, and 4D are top and side views of a sealing device in accordance with various embodiments.
Figure 4B:
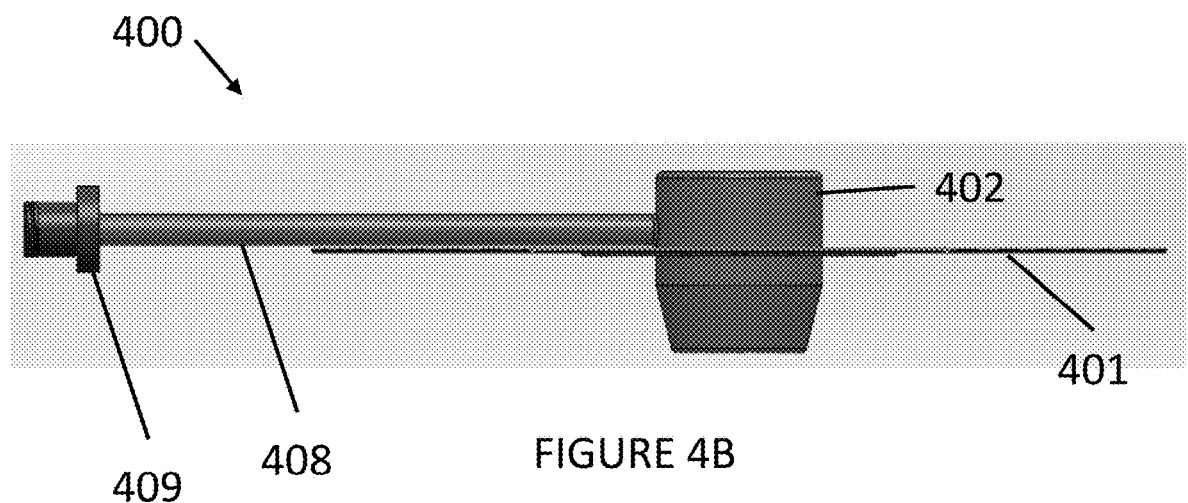
Figure 4C:
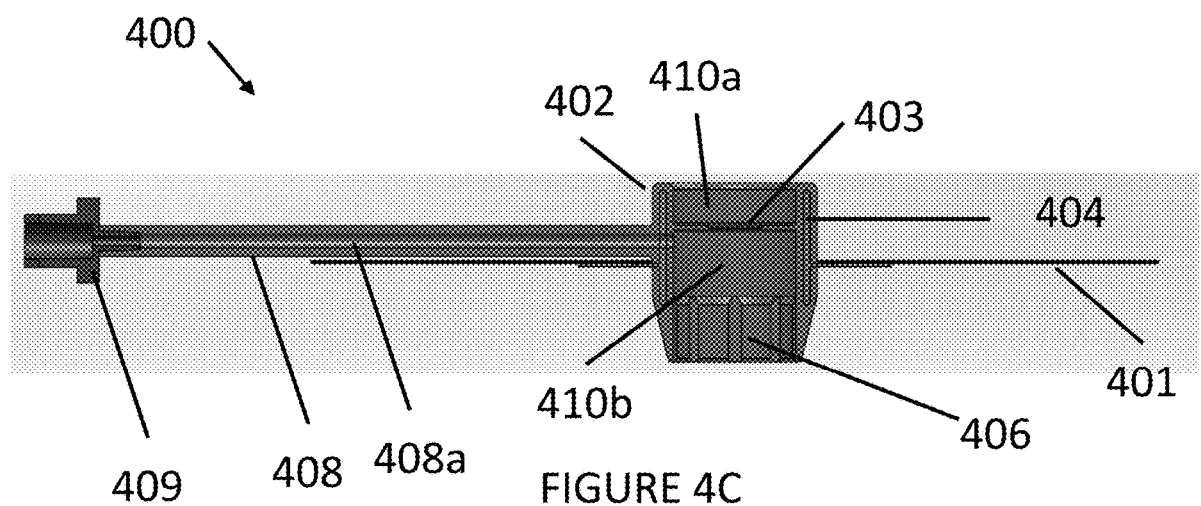

FIGS. 4A-4D illustrate a device 400 for placement at a surgical site to create a substantially tight gas seal. For example, the gas seal can be a substantially gas-tight seal. Referring to FIG. 4A, device 400, in accordance with various embodiments of the present disclosure, can include a body 401, a port 403, and a coupling fitting 409 (e.g., a Luer). The body 401, and coupling fitting 409 can be similar to the body 101, tube 107, and coupling fitting 109 discussed with respect to FIGS. 1A-3G. In some embodiments, the device 400 can include a sealing member 402 and a gas tube 408. The sealing member 402 can be designed to be placed centrally within the body 401 with an opening sized and dimensioned to allow access to the opening of the port 403 through the sealing member 402. The gas tube 408 can be designed to extend from the sealing member 402 in a lateral direction substantially parallel to the body 401. FIG. 4A depicts an above-view of the device 400 including the body 401, the sealing member 402, and the gas tube 408 in relation to one another. As shown in FIG. 4C, the gas tube 408 can include a channel 408a extending along the body 401 having a first opening at one end of the channel 408a (connected to the coupling fitting 409) and a second opening at an opposing end of the channel 408a in fluid communication with the sealing member (e.g., chamber 410b of the sealing member 402) through an opening in the sidewall of the sealing member.

Continuing with FIG. 4A, in some embodiments, the body 401 can be an adhesive pad. The adhesive pad can be constructed from any combination of materials that are sufficiently flexible to conform to the part of the body at which the device 400 is being placed. For example, the adhesive pad can be constructed from a polyurethane material. Similarly, the adhesive material of the adhesive pad can be any combination of adhesive material(s) that allows the body 401 to be removably adhered to the body. For example, the adhesive can be a silicone adhesive, an acrylic adhesive, or any adhesive known in the art including those that are biocompatible. In some embodiments, the adhesive material can be a material that allows the removal and replacement of the device 400 on the patient while still maintaining a sufficient seal, as discussed herein. In particular, the adhesive pad seals the device 400 against the skin of a patient, to avoid leaks coming out of an incision.

To facilitate removal of the device 400, in one embodiment, at least a portion of the body 401 can be provided without adhesive to provide a removal area 410. In some embodiments, the removal area 410 can provide an area for a finger to grip for aiding a user in removing the device 400 from the patient.

Referring to FIG. 4B, a side view of the device 400 with the sealing member 402 attached thereto is provided. The sealing member 402 can be part of the body 401 or can be inserted through the opening in the body 401. As depicted in FIG. 4B, the sealing member 402 can be a substantially cylindrical shape with portions of the sealing member 402 positioned above and below the body 401 of the device 400. As would be appreciated by one skilled in the art, the sealing member 402 can be any combination of shapes, for example, it can be a tubular shape, cylindrical shape, funnel shape, polygonal shape, etc., without departing from the scope of the present invention. The sealing member 402 can be designed to create a seal between the body 401 (adhesive pad) and a surgical instrument 500. In some embodiments, a portion of the sealing member located on the underside of the body 401 can include a tapered shape. The tapered shape can be used for insertion of that portion of the sealing member into an insertion site. In some embodiments, the sealing member 402 can be designed to stretch around a shaft 503 of a surgical instrument 500 to allow insertion of a surgical instrument 500 through the port 403 while maintaining a gas-tight seal when the device 400 is located on a patient. The sealing member 403 can be constructed from any combination of flexible medical grade materials. For example, the sealing member 403 can be made from medical grade silicone. In some embodiments, the sealing member 403 can be coated to allow for easier insertion of the instrument 500 shaft 503. The coating can include any combination of lubrications including, for example, paralyne or Teflon and can be applied using any combination of methods, for example, spraying, dipping, vapor, deposition, etc.

Continuing with FIG. 4B, in some embodiments, the sealing member 402 can be coupled to a gas tube 408. The gas tube 408 can extend from the sealing member 402 in a lateral direction substantially parallel to the body 401. The gas tube 408 can be integrated with the sealing member 402, for example, through injection molding or other manufacturing methods. Alternatively, the gas tube 408 can be a separate piece removably attached to the sealing member 402. In some embodiments, the gas tube 408 can be a substantially cylindrical shape. As would be appreciated by one skilled in the art, the gas tube 408 can be any combination of shapes, for example, it can be a funnel, shape, polygonal shape, etc., without departing from the scope of the present invention.

In some embodiments, the gas tube 408 can be designed to include or otherwise be coupled to the coupling fitting 409. The coupling fitting 409 can be coupled to a first end of the gas tube 408, located opposite to the end of the gas tube 408 coupled to the sealing member 402, for coupling the device 400 to another device (e.g., an insufflation tube). The coupling fitting 409 can include any combination of mechanisms to couple the gas tube 408 to a surgical device or other device. For example, the coupling fitting 409 can be a Luer, a threaded head, a friction fit head, etc., or a combination thereof. In some embodiments, the fluid source can be provided through the port 403, through a lumen incorporated with the device 400, and/or through an separate instrument at a separate point of entry. In some embodiments, the body 401 can be configured for distal insufflation such that the fluid source can be provided through a lumen in a medical instrument separate from the device 400.

Referring to FIG. 4C, in some embodiments, the sealing member 402 can include one or more chambers 410. FIG. 4C depicts a cross-sectional view of the device 400 including the sealing member 402. As shown in FIG. 4C, the sealing member 402 can include a chamber 410a above the port 403 and a chamber 410b below the port 403 with a wall (including an opening for port 403) diving the two chamber 410a, 410b. In some embodiments, the gas tube 408 can be configured to extend through the sealing member 402 sidewall into the lower chamber 410b to create a pathway extending from the connector 409 through the gas tube 408 to the lower chamber 410b of the sealing member 402, as shown in FIG. 4C.

In some embodiments, the sealing member 402 can include one or more channels 406. FIG. 4C depicts a cross-sectional side view of the device 400 with the sealing member 402 attached thereto. The channels 406 can be located within a portion of the sealing member 402, for example, the portion of the sealing member 402 that is located underneath the body 401, as shown in FIG. 4C. Alternatively, the channels 406 can run the full length of the sealing member 402. The channels 406 can be designed to bump up against a shaft 503 of a medical instrument 500 to create a passageway for gas to pass by (via the channel 408a) and avoid a pinch-off situation where the gas can be cut off when the shaft 503 is inserted in the port 403.

Continuing with FIG. 4C, in some embodiments, the device 400 can include a stiffener 404. The stiffener can be configured to maintain a seal for the device 400 when a medical instrument has been inserted into the port 403. In some embodiments, the stiffener 404 can be designed with a substantially cylindrical shape. In some embodiments, during manufacture, the cylindrical portion of the stiffener 404 can be encased within the sealing member 402 to provide reinforce the seal provided by the body 402 so that it does not stretch so much that it distorts and leaks. For example, the stiffener 404 can be a separately molded piece that can be insert molded into the sealing member for encasement, as shown in FIG. 4C. As would be appreciated by one skilled in the art, the stiffener 404 can be any size and shape that is designed to be embedded within, inserted inside, or encased around the sealing member 402 to provide reinforcement to the sealing member 402. To provide the reinforcement, the stiffener 404 can be made from a stiff material, for example, polycarbonate or other plastic or metal material.

Figure 4D:
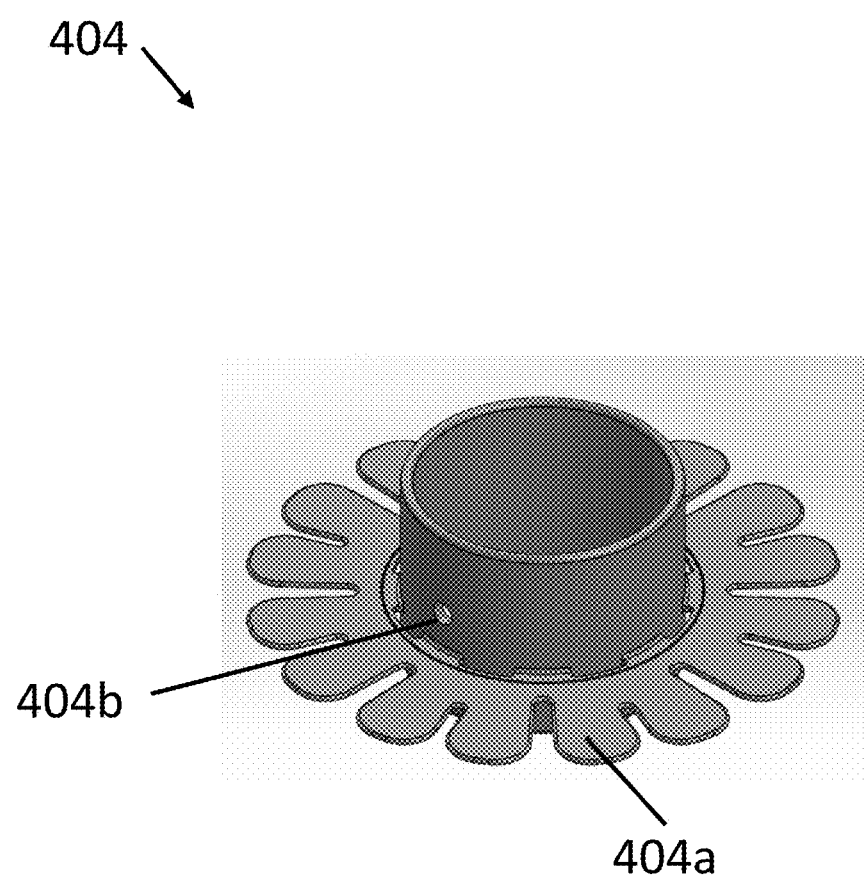

In some embodiments, the stiffener 404 can include one or more of geometric protrusions 404a, for example, fingers, pedal shapes, etc. that extend therefrom to provide support for the sealing member 402, as depicted in FIG. 4D. The geometric protrusions 404a can be designed to extend out from the sealing member 402 underneath and substantially parallel to the body 401, as shown in FIG. 4C. In some embodiments, the geometric protrusions 404a can be flexible enough to bend and flex to conform to the surface of a patient and can be used to create a bonding surface to the adhesive pad of the body 401 to the stiffener 404 and/or the sealing member 402. In some embodiments, the geometric protrusions 404a can be positions on the underside of the body 401, such that it can be sandwiched between the adhesive pad and the target skin. In some embodiments, the adhesive pad can have a removable liner (not depicted) with a special cut out to allow the geometric protrusions 404a of the stiffener 404 to stick to the body 401 during manufacturing. The rest of the liner can stay on the adhesive pad until removed for placement on a patient.

Referring to FIG. 4D, in some embodiments, the stiffener 404 can have a cross hole 404b designed to be coupled to the gas tube 408 to allow gas to pass from the gas tube 408 (e.g. via coupling fitting 409) to the port 403 in the body 401 (e.g., where the gas tube 408 extends through the sidewall of the sealing member 402).

In operation, a surgical instrument 500 can be inserted through the port 403 of the device 400, and the opening in the body 401, to form a gas-sealed fit with the body 401 and advanced to a surgical site to perform a surgical procedure, such as harvesting a vessel. The surgical instrument 500 can be a surgical device as discussed with respect to the surgical devices 200, 300 and can include a tip 501 and a shaft 503. In some embodiments, the tip 501 and the shaft 503 are sized and dimensioned to fit within the sealing member 402 of the device 400.

Figure 5A:
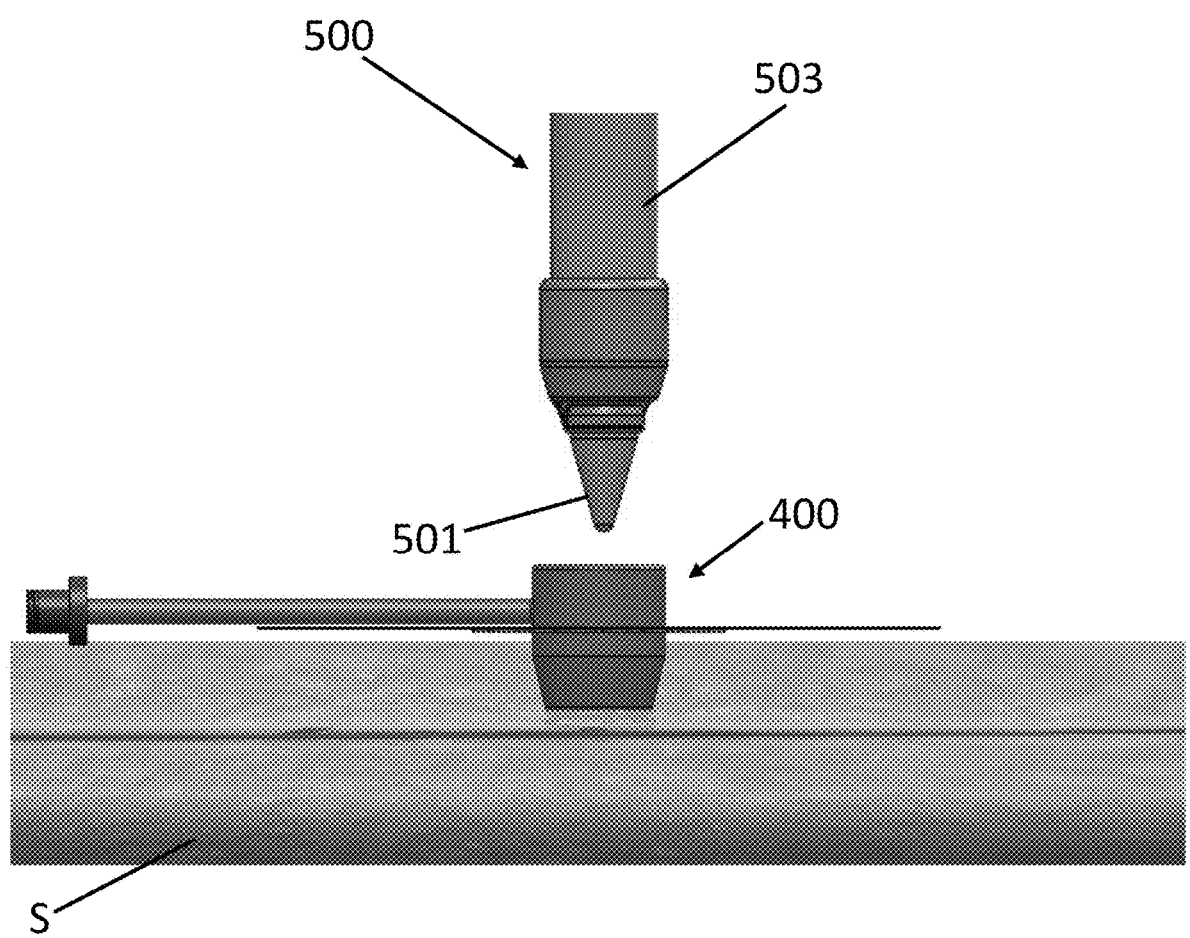
FIGS. 5A and 5B are diagrams illustrating steps for another method of using the sealing device of FIGS. 4A, 4B, 4C, and 4D in accordance with various embodiments.

Referring to FIG. 5A, in some embodiments, the device 400 can be used with a surgical instrument 500 to perform a cut-down procedure, as discussed in greater detail with respect to FIGS. 2A-2F. During a cut-down procedure using device 400, a user can make an incision and find a vein, doing some light proximal dissection to open the space a little under direct visualization. When a vein is found, the user can peal the liner from the adhesive pad off the underside of the body 401 and insert at least a portion of the sealing member 402 into the insertion site of the patient, as shown in FIG. 5A. With at least a portion of the sealing member 402 inserted, the adhesive pad of the body 401 can be placed onto and adhered to a surface of the skin at the incision site to create a gas-tight skin seal at the insertion site. Thereafter, the user can hook up a gas source to the connector 409 and gas can be provided to the insertion site through the gas tube 408 and port 403. When the procedure is done, the user can peal the adhesive pad off the patient and discard or clean the device 400 for reuse.

Figure 5B:
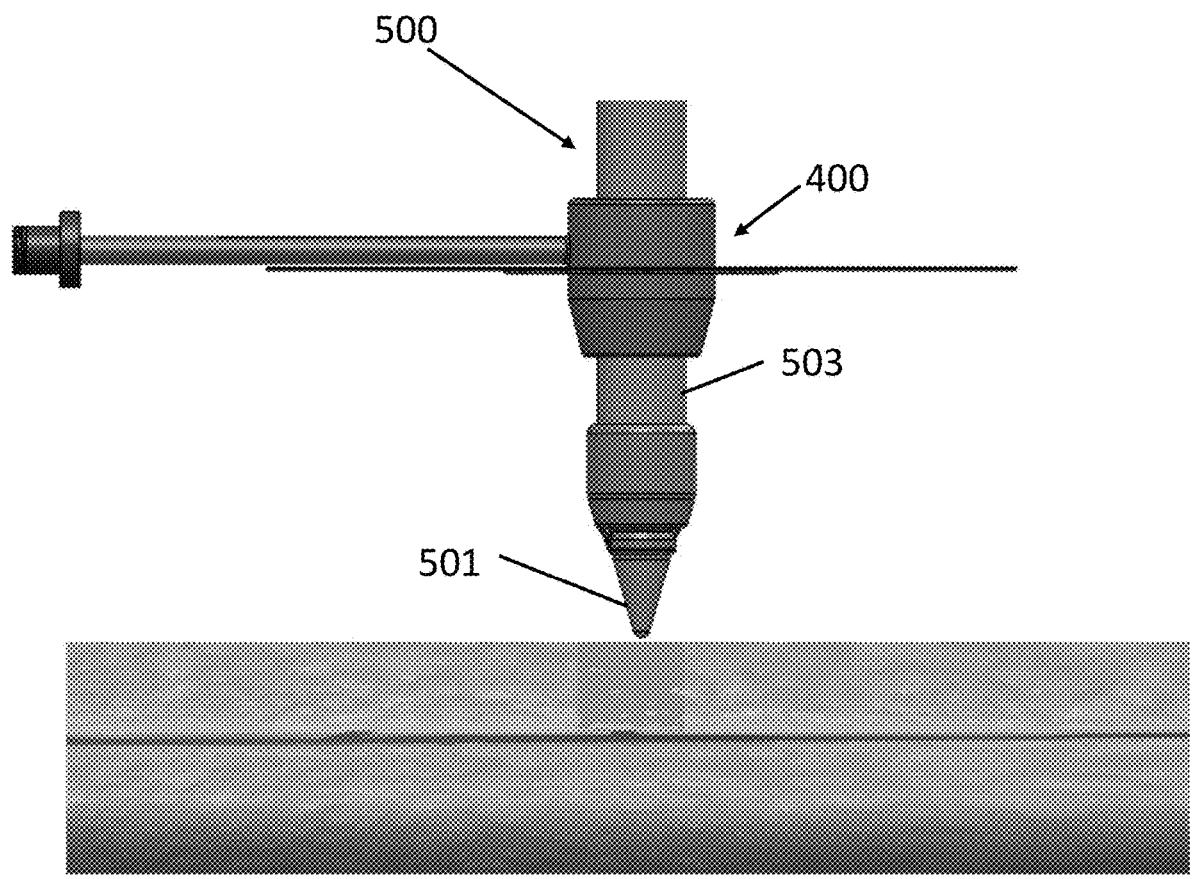

Referring to FIG. 5B, in some embodiments, the device 400 can be used with a surgical instrument 500 to perform a tip-search procedure, as discussed in greater detail with respect to FIGS. 3A-3F. During the tip-search procedure using device 400, a user can make a small incision near a vein, then using the surgical instrument 500, look through a camera (e.g., within tip 501) to find the vein. Under a tip-search, the vein can be found, not under direct visualization, but through a normal camera. As depicted in FIG. 5B, the device 400 can be combined with the surgical instrument 500 prior to beginning the tip-search. Once the user locates the target vein, the user can peal the liner off the adhesive pad and slide the device 400 down the shaft 503 of the surgical instrument 500 until the adhesive pad makes contact with the skin, adhering to the skin and creating the seal. Thereafter, the user can hook up a gas source to the connector 409 and gas can be provided to the insertion site through the gas type 408 and port 403. When the procedure is done, the user can peal the adhesive pad off the patient and discard or clean the device 400 for reuse.

In operation, the device(s) of the present invention provide systems and methods for providing a gas-tight seal at a surgical site while providing access to the surgical site through a port, as discussed with respect to FIGS. 1A-5B. Initially, to form the gas-tight seal, the body of the device can be placed over a surgical site so that the port is substantially in alignment with an incision point at the surgical sit. The flexibility of the pad, when placed on the surface of the surgical site, allows the pad to contour about the site to create a substantially gas-tight seal. To enhance adherence of the pad to the surgical site, an adhesive layer of the pad can be placed in contact with a surface of the surgical site.

With the pad secured to the surgical site, the port of the device can be utilized to insert an appropriate surgical instrument(s). The port can be sized and dimensioned to receive the surgical instrument while maintaining the gas-tight seal at the surgical site. In particular, the surgical instrument can be inserted through and engage with the port during entry. With the surgical instrument placed through the port toward the surgical site, a number of tasks can be performed. The tasks include, but are not limited to, accessing a target anatomical structure within the surgical site (e.g., via tip of the instrument), communicating a fluid flow into the surgical site, harvesting/removing material from the surgical site, incising at the surgical site, or a combination thereof. The introduction of the fluid flow (e.g., insufflation gas) can be performed distally from the pad, through the port of the pad via the surgical instrument itself, and/or through a lumen/tube of the pad.

Once the surgical procedure has been completed, the pad can be removed from the surgical site with minimal impact on the surface of the surgical site. For example, the pad can be removed by grasping and pulling a tab extending from the pad or a portion of the pad that is void of adhesive. The pad, or portions thereof, can then be discarded or cleaned for reuse.

While the present disclosure has been described with reference to certain embodiments thereof, it should be understood by those skilled in the art that various changes may be made and equivalents may be substituted without departing from the true spirit and scope of the disclosure. In addition, many modifications may be made to adapt to a particular situation, indication, material and composition of matter, process step or steps, without departing from the spirit and scope of the present disclosure. All such modifications are intended to be within the scope of the claims appended hereto.

What is claimed is:

1. A method comprising:
   identifying a surgical site having an incision;
   placing a flexible body against the surgical site such that the flexible body engages the surgical site across an entire bottom surface of the flexible body to form a gas seal between the bottom surface of the flexible body and the surgical site; and
   inserting a surgical instrument through a port, disposed through the flexible body, into the incision at the surgical site while maintaining a gas-sealed engagement with the surgical instrument.

2. The method of claim 1, wherein the step of placing further comprises, adhering the flexible body to the surgical site with an adhesive disposed on the bottom surface of the flexible body.

3. The method of claim 2, wherein the step of adhering includes disposing the adhesive over the entire bottom surface of the flexible body.

4. The method of claim 1, wherein, in the step of placing, the flexible body includes one of a flap, a septum, a one-way valve, or combinations thereof for sealing the port when no surgical instrument is present therein.

5. The method of claim 1 further comprising:
   deforming the port elastically to form a gas sealed fit with the surgical instrument.

6. The method of claim 1 further comprising:
   grasping a tab extending from the flexible body; and
   pulling the tab to remove the flexible body from the surgical site.

7. The method of claim 1 further comprising:
   delivering a fluid flow through the flexible body into the surgical site.

8. The method of claim 1 further comprising:
   suctioning a fluid flow from the surgical site through the flexible body.

9. The method of claim 1 further comprising:
   cutting the incision at the surgical site.

10. A method comprising:
    engaging a flexible body against a surgical site so that an entire bottom surface of the flexible body forms a gas seal with the surgical site;
    inserting a surgical instrument through a port, disposed through the flexible body, into an incision at the surgical site while maintaining a gas-sealed engagement with the surgical instrument; and performing a surgical procedure using the surgical instrument.

11. The method of claim 10, wherein the step of engaging further comprises,
adhering the flexible body to the surgical site with an adhesive disposed on the bottom surface of the flexible body.

12. The method of claim 11, wherein the step of adhering includes disposing the adhesive over the entire bottom surface of the flexible body.

13. The method of claim 10, wherein, in the step of engaging, the flexible body includes one of a flap, a septum, a one-way valve, or combinations thereof for sealing the port when no surgical instrument is present therein.

14. The method of claim 10 further comprising:
deforming the port elastically to form a gas-sealed fit with the surgical instrument.

15. The method of claim 10 further comprising:
advancing a tip of the surgical instrument to a target tissue.

16. The method of claim 15 further comprising:
dissecting tissue surrounding the target tissue away from the target tissue.

17. The method of claim 10 further comprising:
grasping a tab extending from the flexible body; and
pulling the tab to remove the flexible body from the surgical site.

18. The method of claim of 10 further comprising:
aligning the port with the incision on the surgical site.

19. The method of claim 10 further comprising:
removing the surgical instrument through the port while maintaining a gas-sealed environment.

20. The method of claim 10, wherein, in the step of inserting, the surgical instrument is a tissue harvester.

* * * * *